(12) United States Patent
Brögger et al.

(10) Patent No.: US 10,656,723 B2
(45) Date of Patent: May 19, 2020

(54) APPARATUS FOR EXTRACORPOREAL BLOOD TREATMENT COMPRISING ALL-ROUND DISPLAY

(71) Applicant: B. BRAUN AVITUM AG, Melsungen (DE)

(72) Inventors: Sebastian Brögger, Knüllwald (DE); Armin Riess, Melsungen (DE)

(73) Assignee: B. Braun Avitum AG (DE)

( * ) Notice: Subject to any disclaimer, the term of this patent is extended or adjusted under 35 U.S.C. 154(b) by 9 days.

(21) Appl. No.: 15/829,158

(22) Filed: Dec. 1, 2017

(65) Prior Publication Data

US 2018/0157335 A1 Jun. 7, 2018

(30) Foreign Application Priority Data

Dec. 2, 2016 (DE) .......................... 10 2016 123 371

(51) Int. Cl.
*G09G 5/00* (2006.01)
*G06F 3/01* (2006.01)
(Continued)

(52) U.S. Cl.
CPC ............ *G06F 3/017* (2013.01); *A61B 5/1113* (2013.01); *A61B 5/1176* (2013.01); *A61M 1/14* (2013.01); *A61M 1/36* (2013.01); *F16M 11/128* (2013.01); *G06F 3/011* (2013.01); *G06F 3/1423* (2013.01); *G06F 3/1431* (2013.01); *G06F 9/4451* (2013.01); *G06K 9/00255* (2013.01); *G06K 9/00335* (2013.01); *G08B 3/10* (2013.01);
(Continued)

(58) Field of Classification Search
CPC ............................... F16M 11/128; A61M 1/14
USPC ........................................................ 345/156
See application file for complete search history.

(56) References Cited

U.S. PATENT DOCUMENTS

2007/0180129 A1 8/2007 Tolmie et al.
2010/0271296 A1* 10/2010 Kopychev ............... A61M 1/14
345/156
(Continued)

FOREIGN PATENT DOCUMENTS

DE 102012109861 A1 4/2014
EP 2857053 A1 4/2015
JP H09107514 A 4/1997

OTHER PUBLICATIONS

German Search Report for German Application No. 10 216 123 371.4, with translation, dated Jun. 27, 2017, 12 pages.
(Continued)

*Primary Examiner* — Abdul-Samad A Adediran
(74) *Attorney, Agent, or Firm* — RatnerPrestia

(57) ABSTRACT

An apparatus for extracorporeal blood treatment comprising a control unit and a display device, wherein the apparatus for extracorporeal blood treatment is equipped with a person locating and identifying device and the person locating and identifying device and the display device are in contact of information exchange with each other via the control unit and the person locating and identifying device is adapted to obtain and to process information about the position of a person being located in the environment of the apparatus for extracorporeal blood treatment, and the display device is adapted to display on a display information in response to the position of the person so that it is visible from the position of the person.

11 Claims, 3 Drawing Sheets

(51) Int. Cl.

| | | |
|---|---|---|
| *A61M 1/14* | (2006.01) | |
| *G06F 3/14* | (2006.01) | |
| *G09G 3/00* | (2006.01) | |
| *G16H 40/63* | (2018.01) | |
| *G16H 10/65* | (2018.01) | |
| *G16H 20/17* | (2018.01) | |
| *F16M 11/12* | (2006.01) | |
| *A61B 5/11* | (2006.01) | |
| *A61B 5/1171* | (2016.01) | |
| *A61M 1/36* | (2006.01) | |
| *G06F 9/445* | (2018.01) | |
| *G06K 9/00* | (2006.01) | |
| *G08B 3/10* | (2006.01) | |

(52) U.S. Cl.
CPC ............... *G09G 3/003* (2013.01); *G09G 5/00* (2013.01); *G16H 10/65* (2018.01); *G16H 20/17* (2018.01); *G16H 40/63* (2018.01); *A61M 2205/18* (2013.01); *A61M 2205/3306* (2013.01); *A61M 2205/502* (2013.01); *A61M 2205/581* (2013.01); *G09G 2340/0407* (2013.01); *G09G 2340/0464* (2013.01); *G09G 2340/14* (2013.01); *G09G 2354/00* (2013.01); *G09G 2380/08* (2013.01)

(56) References Cited

U.S. PATENT DOCUMENTS

| | | |
|---|---|---|
| 2010/0274582 A1 | 10/2010 | Beraja et al. |
| 2013/0317837 A1 | 11/2013 | Ballantyne et al. |
| 2014/0102957 A1 | 4/2014 | Broeker et al. |
| 2015/0002490 A1 | 1/2015 | Han et al. |
| 2016/0152370 A1 | 6/2016 | Bergers et al. |
| 2017/0168688 A1 | 6/2017 | Yuds |
| 2017/0278477 A1* | 9/2017 | Jeong .................. F16M 11/128 |

OTHER PUBLICATIONS

European Search Report for European Application No. 17 204 402.6, dated Apr. 9, 2018, including English translation, 18 pages.

* cited by examiner

APPARATUS FOR EXTRACORPOREAL BLOOD TREATMENT COMPRISING ALL-ROUND DISPLAY

CROSS REFERENCE TO RELATED APPLICATIONS

This application claims priority to German application DE 10 2016 123 371.4 filed Dec. 2, 2016, the contents of such application being incorporated by reference herein.

FIELD OF THE INVENTION

The invention relates to an apparatus for extracorporeal blood treatment, for example a dialysis machine, comprising an integrated or external display device displaying information of the machine, for example feedback about the status of the treatment cycle, of the maintenance or the machine condition, to the user, and to an apparatus for extracorporeal blood treatment according to the preamble of the independent claim.

BACKGROUND OF THE INVENTION

At present, apparatuses for extracorporeal blood treatment include display devices that are mounted statically or rotatably and pivotally thereon and are manually mechanically operable by the user such as e.g. medical specialized staff, technicians or patients using home dialysis, by operating elements such as buttons or via a touchscreen. Accordingly, the alignment of the display is independent of the spatial position of the user.

In a fixed static arrangement of the display area according to a known state of the art the visibility of the displayed information is strongly restricted for the users and their range of manual interaction during usual operation, as for reading the information and/or for operating the apparatus for extracorporeal blood treatment they have to find themselves directly in front of the fixedly installed display device. Therefore, the restriction of the display visibility and of the range of manual interaction constitutes a considerable drawback especially to the clinical staff such as physicians and nursing staff, who during normal hospital operations simultaneously care for plural blood treatment processes. Thus, the visibility of the displayed information frequently is not possible for the patient either. The invariant manual range interaction for operating the apparatus for extracorporeal blood treatment is disadvantageous also to a service technician who maintains the apparatuses for extracorporeal blood treatment, as it impedes simultaneous operation of plural machines.

Apparatuses for extracorporeal blood treatment comprising a rotatable and pivotal display device according to another known state of the art improve the handling of one or more machine cycles in so far as the display can be manually aligned to the position of the user. However, also with the machines comprising a rotatable/pivotal display device it is required to act within the range of manual interaction and information can be read only frontally ahead of the display device. A dynamic adaptation of the alignment of the display device to the position of the user and a machine-user interaction outside the range of manual interaction is not possible.

This constitutes a problem especially in a case in which plural machines for extracorporeal blood treatment are simultaneously signaling a critical situation, as the user first has to enter the respective range of display visibility of all alarming machines in order to decide which machine requires the first intervention.

SUMMARY OF THE INVENTION

Therefore, it is an object of aspects of the present invention to solve the afore-mentioned problems of the known display devices on an apparatus for extracorporeal blood treatment, e.g. a dialysis machine, and to design a display device that ensures improved readability and especially enables to the users, irrespective of their spatial position relative to the machine, the visibility of the displayed information of the machine and a machine-user interaction outside the range of manual interaction, i.e. the range within which the users may establish direct manual contact for operating the machine.

This object is achieved, according to aspects of the invention, by the combination of features of the independent claim. Advantageous developments/embodiments of the invention are the subject matter of the enclosed subclaims.

Thus, it is a basic idea of aspects of the invention to equip an apparatus for extracorporeal blood treatment with at least one display device and at least one person locating/identifying device and, respectively, function so that the at least one display device displays the information to be displayed dynamically toward the position of the user/person, i.e. tracks the movements of the user/person in the room, respectively within a defined environment around the apparatus for extracorporeal blood treatment, so that the information is visible on the display device from the position (location) of the user/person. In other words, the display direction for the information to be displayed orientates itself by the current position and by the user's movement in the room, respectively within the defined environment around the apparatus for extracorporeal blood treatment, (change of position) and is aligned and guided toward the user. Moreover, the apparatus for extracorporeal blood treatment may optionally be equipped with a further sensor system which obtains and processes information about the user's gestures (movements of the user at the current position in the room, respectively within the defined environment around the apparatus for extracorporeal blood treatment) and thus permits a machine-user interaction outside the range of manual interaction of the user (arm reach) by his/her control gestures within a sensory range of interaction (machine-user interaction).

More concretely speaking, the apparatus for extracorporeal blood treatment includes the afore-mentioned display device, the person locating/identifying device as well as a controller (computer) that receives signals of the person locating/identifying device and therefrom computes the current position of the user relative to the apparatus of extracorporeal blood treatment. Said computing may include establishing the current angle (cardinal direction) relative to the apparatus for extracorporeal blood treatment and/or the distance from the apparatus for corporeal blood treatment. Depending on the computing results, the controller controls the display device so as to align the display direction thereof to the position of the user. For this, the display device may include e.g. an electrically driven rotor which appropriately rotates e.g. a monitor at least about a vertical axis, or the display device may be in the form of an all-round display, with the direction of information being electronically aligned to the user's position on the all-round display.

In the case of optional/additional distance measurement, depending on the computing result the information can be presented in large(r) or small(er) size.

In the case of an optional/additional gesture identifying function, depending on detected/identified movements of the user at the already detected position of the user individual/selected functions of the apparatus for extracorporeal blood treatment can be activated/deactivated/set in a control-based manner.

The advantages of an apparatus for extracorporeal blood treatment comprising such display device and person locating/identification reside in the immediate position-independent visual inspection of displayed information and the option of immediate (so-to-speak remote-controlled) position-independent operation of the apparatus for extracorporeal blood treatment (hereinafter referred to as dialysis machine) by the user so that in a case in which plural machines simultaneously output an alarm signal the actions can be quickly prioritized. Thus, the present invention enables both increased safety for patients in the case of alarm and uncomplicated attendance to the treatment cycles simultaneously on plural machines.

Further, an object is achieved by an apparatus for extracorporeal blood treatment comprising a control unit (controller) and a display device, wherein the apparatus for extracorporeal blood treatment is equipped/configured with a person locating/identifying device and the person locating/identifying device and the display device are in contact for exchange of information with each other via the control unit and the person locating/identifying device is adapted to obtain and to process information about the current position of a person being in the environment of the apparatus for extracorporeal blood treatment, and wherein the display device is adapted to display information on a display, which is preferably visible from all positions inside the range detectable by the person locating/identifying device, depending on the current position of the person, especially relative to the apparatus for extracorporeal blood treatment, preferably automatically in the direction of the position of the person, so that it (the information) is visible from the person's position.

In other words, the person locating/identifying device associated with an apparatus for extracorporeal blood treatment detects a person within a defined environment of said apparatus (corresponding to the detecting capacity of a sensor used) for extracorporeal blood treatment and the control unit preferably being part of the apparatus for extracorporeal blood treatment controls the display device whose display is visible from all positions inside the defined environment so that the information to be displayed is automatically displayed toward the position of the person within the defined environment. The defined environment around the apparatus for extracorporeal blood treatment is understood to be the entire range detected by the sensor system of the person identifying device.

Advantageously, the user of the apparatus for extracorporeal blood treatment, which includes physicians, nursing staff, technicians or patients, is identified as person by the person locating/identifying device in such configuration of the apparatus for extracorporeal blood treatment and the information to be presented on the display of the display device is displayed automatically in the direction of the position of the person and is tracked depending on the person's movement so that the user may move independently of the arrangement of the display on the machine inside the treatment room without losing the visual contact to the displayed information about the treatment cycle and/or the machine condition. Such display device may be e.g. cylindrical or polyhedral including an external peripheral display, wherein it is also possible to dispose plural display surfaces so as to form an overall display surface. There may also be arranged buttons for manual operation of the display device on the display device, and the integration of a touchscreen for operating the display is possible as well. In another configuration of the display device according to aspects of the invention, plural displays are disposed at different positions of the room so that at least one display is visible from each position in the room. The dynamic adaptation of the displaying direction depending on the position of the user renders manual intervention for adjusting the displaying direction unnecessary, thus also a distance of the user from the range of manual interaction constituting no limitation to the immediate visual inspection of displayed information. This renders the user capable of carrying out further jobs, e.g. the operation of another machine, in the environment of the apparatus for extracorporeal blood treatment, without restricting check on a safe implementation of the treatment cycle on the apparatus for extracorporeal blood treatment.

Preferably, the person locating/identifying device is provided and adapted to obtain and to process information about the person's gestures, and the display device is adapted to be operable by the information about the person's gestures.

As an alternative, the person locating/identifying device comprises a separate sensor system being provided and adapted to obtain and to process information about gestures of the person, and the display device is adapted to be operable by the information about the person's gestures.

Operating the display device by gestures enables the users to operate the display outside the range of manual interaction. In this way, they can ensure quick adaptation of the presentation, e.g. type size or switchover of the information menu without having to change their position inside the room. A possibility of operating the dialysis machine by gestures outside the range of manual interaction means considerable facilitation to the users, as they can react also from a distance at which immediate manual intervention is not possible. Especially in situations in which critical alarm is reported on a machine, a possibility of immediate reaction serves for the patient's safety. Moreover, a range of sensory interaction exceeding the range of manual interaction enables the user to handle plural therapeutic processes in parallel in a more clear-cut manner.

Of further preference, the apparatus for extracorporeal blood treatment can be operated with user profiles each being associated with a user identity, and the person identifying device is adapted to obtain and process information about a user identity of the person and the display device is provided and adapted to display information depending on the user identity of the person according to the pertinent user profile on a display, and the display device and/or the dialysis machine is/are provided and adapted to be operable in response to the user identity of the person according to the pertinent user profile.

In such configuration, it is possible when operating the apparatus for extracorporeal blood treatment to automatically assign personal display settings, e.g. size, brightness, optical sorting of groups of information etc., and user-dependent authorizations for operating the machine to individual users. In the normal case, the authorizations for carrying out particular changes and settings, e.g. drafting a treatment cycle, changing a treatment cycle or intervening in a current treatment cycle, will be different amount user groups such as physicians, nursing staff and technicians. By adopting display settings dependent on the user, the user's operating convenience is increased. A person identifying device which is capable of performing an identity determination of the person within the range of sensory interaction of the machine moreover may ensure that exclusively operating functions to which the user is authorized can be carried out. Such user identity recognition helps to prevent any situation in which a first user is logged into the machine and a second user from the vicinity of the machine performs an operation with the authorizations of the first user. This protects access to the treatment cycle against unauthorized persons and constitutes another measure for increasing the patient's safety. A simple possibility of determining the identity is offered by the read-out of a chip which is integrated, for example, in carried badges of the clinical staff or in the guest card or in the patient's chip card and can be read out by the person identifying device.

It is further preferred that the person identifying device includes at least one camera. A camera offers a well-known inexpensive sensor system by which person identification can be facilitated. It is especially preferred that the person identifying device includes a face identifying device. Face identification offers another option of determining the identity of a user in the vicinity of the apparatus for extracorporeal blood treatment and replaces carrying a badge for operating the machine. Moreover, the face identification is superior to a carried chip card in so far as interchanging of badges may result in the fact that a user being in possession of a foreign chip card will operate the machine with authorizations to which he/she is not authorized. Also, the risk of a badge getting lost unnoticed and an operation of the machine being blocked in this way is eliminated by face identification.

Preferably, the apparatus for extracorporeal blood treatment is equipped with a device for acoustic alarm, for example a siren, and the person identifying device and the device for acoustic alarm are in contact of information exchange with each other and the device for acoustic alarm is provided and adapted to be operable by signals of the person identifying device.

It is ensured by an acoustic alarm on the apparatus for extracorporeal blood treatment that also a user outside the visual range or a user turned away from the display can be alarmed. This is of advantage especially in the case of highly critical errors so as to obtain quick reaction by the clinical staff. The connection of the device for acoustic alarm and the person identifying device helps to automatically inactivate the alarm when the authorized user interferes with the therapeutic process by gestures.

Moreover, it is preferred that the display device includes a display having a convexly bent display surface facing away from the center of curvature. A display of such shape can be viewed from the user from plural positions in the room, depending on the radius of curvature and the circumference a display of said shape is visible from all positions in the room. Thus, information on the curved display can always be automatically displayed toward the position of the user so that the information can always be seen by the user without any active intervention by the user being required. It is not mandatory for the curvature of the display surface to enclose 360°, also an opening toward the rear side of the machine is of advantage, as a machine including such display device can be properly integrated in a small room on the wall side.

Of preference, the display device is adapted to display a criticality assessment in the case of alarm. This permits the user to immediately decide on the urgency of action, especially in the case of alarms simultaneously on plural machines.

Further preferred is a network of plural apparatuses for extracorporeal blood treatment comprising the afore-described features, wherein the display devices of the apparatuses for extracorporeal blood treatment are adapted to display, in the case of parallel alarms on plural machines, the information to be displayed on the display surfaces of the display devices in accordance with the priority of the alarms.

Automated prioritization of parallel alarms renders the user ready to act for immediate troubleshooting, as the preceding required analysis of urgency of the errors reported in parallel is omitted in such network. Thus, a critical error can be ensured to be eliminated within minimum time and the patient's safety can be ensured to be further increased.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
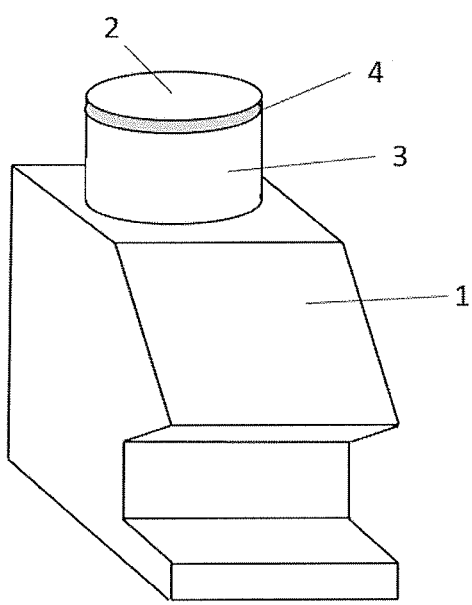
FIG. 1 shows a simplified representation of an apparatus for extracorporeal blood treatment according to aspects of the invention comprising a display device having an external convexly curved display and comprising a person identifying device.

FIG. 1 illustrates a simplified representation of an apparatus for extracorporeal blood treatment 1 comprising a display device 2 in the present case having an external convexly curved display 3 and a person locating/identifying device 4. The display device 2 is preferably disposed in the upper area of the apparatus for extracorporeal blood treatment 1 (dialysis machine) so that it is within the viewing range of the user. The surface of the curved display 3 on the display device 2 is convexly curved and is turned away from the center of curvature so that it faces the user in the perimeter (preferably 360°) of the apparatus for extracorporeal blood treatment 1 from all positions in the room, where appropriate. In the preferably upper area of the display device 2 the person locating/identifying device 4 is provided the sensor system of which covers the (complete) perimeter of the apparatus for extracorporeal blood treatment 1. The position of a person in the perimeter of the apparatus for extracorporeal blood treatment 1 is detected by the person locating/identifying device 4 and the detection signals of a controller/control unit/computer are preferably supplied to the apparatus for extracorporeal blood treatment 1. Since apparatuses for extracorporeal blood treatment 1 already belong to the state of the art and, as is known, they are always equipped with a control unit for controlling/regulating the functions internal to the apparatus, a more detailed description of such apparatus as well as of the control thereof can be dispensed with here; instead, the relevant state of the art, for example to the applicant of this application, can be referred to. The controller controls the display device 2 in such way that the information to be displayed can always be displayed in the direction of the user via the curved display thereof.

Figure 2:
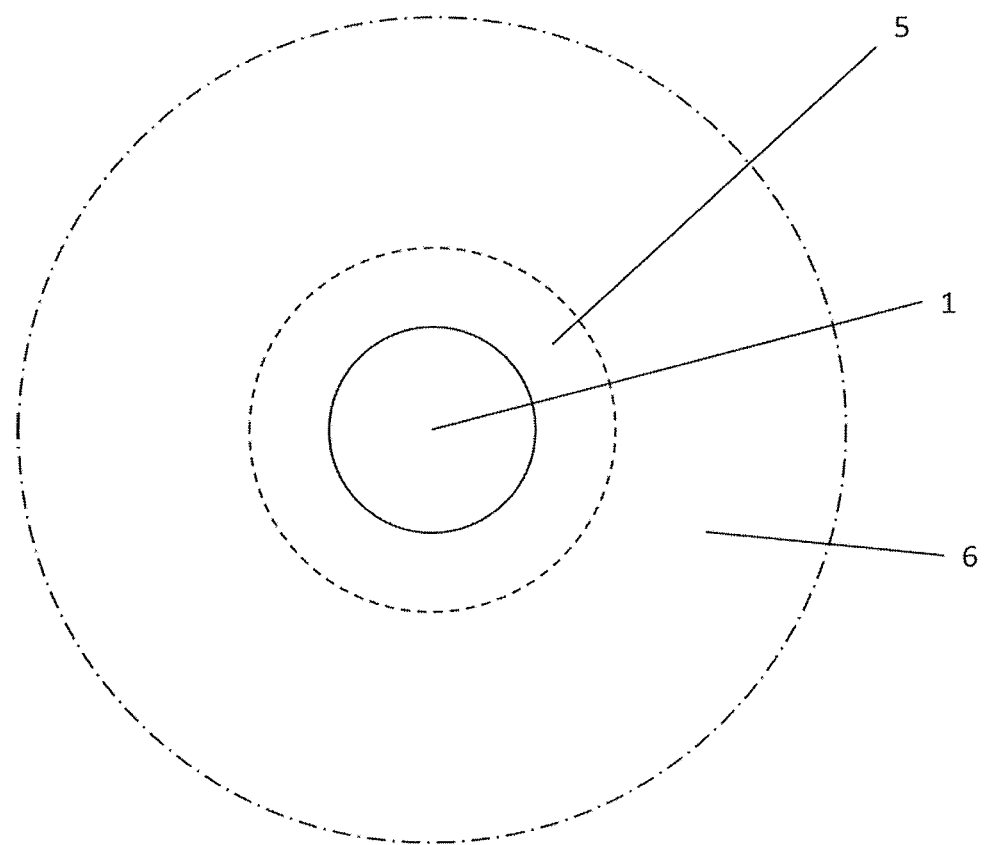
FIG. 2 shows a schematic representation of the ranges of interaction around the apparatus for extracorporeal blood treatment.

FIG. 2 illustrates a schematic representation of the ranges of interaction around the apparatus for extracorporeal blood treatment 1. The range of manual interaction 5 (average arm length) is the range indicated by the broken line around the apparatus for extracorporeal blood treatment 1 in which the user can establish direct contact with the apparatus for extracorporeal blood treatment 1 so as to manually operate e.g. actuating elements such as buttons and switches on the machine or the display device 2 or a touchscreen on the display device 2. The range of sensory interaction 6 indicated by a dash-dot line extends from the apparatus for extracorporeal blood treatment 1 beyond the range of manual interaction. Within the range of sensory interaction 6 the user is identified by the person identifying device 4 (not shown in FIG. 2) and the information displayed via the display device 2 is displayed in the direction of the user. Within the range of sensory interaction 6 e.g. gestures and/or the user identity of the user can be detected by the person locating/identifying device 4 so that the user can operate the apparatus for extracorporeal blood treatment 1 and/or display device 2 within the range of sensory interaction 6 contactless in a manner preferably selected/individually reduced to the user.

Figure 3:
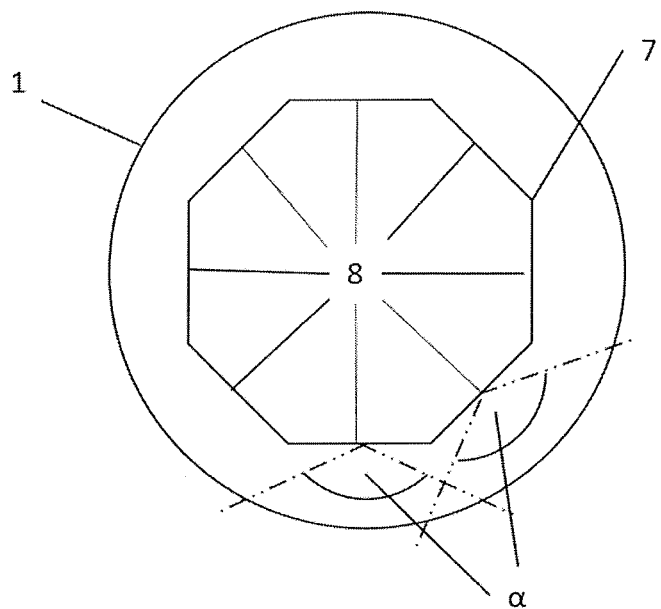
FIG. 3 shows a simplified top view of a display device comprising a polyhedral display and plural display subareas each having a viewing angle α.

FIG. 3 illustrates a simplified top view onto a display device 2 including a polyhedral display 7 and plural display subareas 8 each having a viewing angle α. The polyhedral shape is realized by planar adjacent display subareas 8 facing away from the center of the polyhedron and being orientated to different directions of the room. The viewing angle α is chosen so that from each position within the perimeter around the apparatus for extracorporeal blood treatment 1 at least one display subarea 8 can be seen by the user. For reasons of simplification, the viewing angle α was indicated at one display subarea 8 only.

Figure 4:
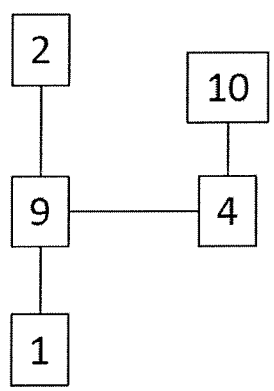
FIG. 4 shows a schematic representation of the apparatus for extracorporeal blood treatment comprising machine components according to aspects of the invention.

FIG. 4 illustrates a schematic representation of the apparatus for extracorporeal blood treatment comprising machine components according to aspects of the invention. The apparatus for extracorporeal blood treatment 1 is equipped with a control unit 9 being connected to the display device 2 and the person locating/identifying device 4. The person locating/identifying device 4 is preferably equipped with a face recognition device 10. Signals that are detected/generated by the sensor system of the person locating/identifying device 4, for example the position of a person in the environment of the apparatus for extracorporeal blood treatment 1, the gestures and/or user identity thereof, where appropriate, and signals of the related face recognition device 10, where appropriate, are forwarded to the control unit 9. In response to the signals of the person locating/identifying device 4, the control unit 9 controls the display of the information on the display device 2, for example in response to the current position of the person detected by the person locating/identifying device 4 in the environment of the apparatus for extracorporeal blood treatment 1 the display direction of the information to be displayed on the display of the display device 2 is controlled. Equally, signals are forwarded from the apparatus for extracorporeal blood treatment 1 to the control unit 9 which, in response to the transmitted information from the apparatus for extracorporeal blood treatment 1, controls the information to be displayed by the display device 2. Also, the user-dependent authorizations for operating the apparatus for extracorporeal blood treatment 1 and the display device 2 are controlled by the control unit 9. For this purpose, the user identity is detected by the user identifying device 4, for example by reading out a person-related chip, or by face recognition by the face recognition device 10 and is forwarded to the control unit 9 which, in response to the pertinent user profile stored on the control unit 9, admits or blocks the operating inputs of the user.

The invention claimed is:

1. A system comprising:
   an apparatus for extracorporeal blood treatment;
   a control unit for the apparatus;
   an external peripheral display fixedly mounted to the apparatus such that the external peripheral display is not movable relative to the apparatus, the external peripheral display having a plurality of subareas directed in different directions; and
   a person locating and identifying device configured to exchange data with the external peripheral display via the control unit, and adapted to obtain and to process location information about a position of a person located in a detectable range;
   wherein the external peripheral display is visible from all positions inside the detectable range, and is adapted to automatically display information about at least one of a treatment cycle and the apparatus, in response to at least the position of the person relative to the apparatus, on a subarea of the external peripheral display facing in a direction of the person so that the displayed information about the at least one of the treatment cycle and the apparatus is visible to the person.

2. The system according to claim 1, wherein the person locating and identifying device is adapted to obtain and to process gesture information about gestures of the person and wherein the external peripheral display is adapted to operate in response to the gesture information.

3. The system according to claim 1, wherein the person locating and identifying device is adapted to obtain and to process gesture information about gestures of the person and wherein the apparatus is adapted to operate in response to the gesture information.

4. The system according to claim 1, wherein the apparatus for extracorporeal blood treatment is operable with a plurality of user profiles, wherein each of the plurality of user profiles is assigned to a user identity, wherein the person locating and identifying device is adapted to obtain and to process identity information about a respective user identity of the person, and wherein the external peripheral display is adapted to display the identity information about the respective user identity of the person according to a pertinent user profile for the person on the display.

5. The system according to claim 1, wherein the apparatus for extracorporeal blood treatment is operable with a plurality of user profiles, wherein each of the plurality of user profiles is assigned to a user identity, wherein the person locating and identifying device is adapted to obtain and to process identity information about a respective user identity of the person, and wherein at least one of the external peripheral display or the apparatus for extracorporeal blood treatment is adapted to operate in response to the respective user identity of the person according to a pertinent user profile for the person.

6. The system according to claim 1, wherein the person locating and identifying device includes a camera.

7. The system according to claim 1, wherein the person locating and identifying device includes a face recognition device.

8. The system according to claim 1, wherein the apparatus for extracorporeal blood treatment is equipped with a device for acoustic alarm, wherein the person locating and identifying device and the device for acoustic alarm exchange information via the control unit, and wherein the device for acoustic alarm is adapted to be operable by signals of the person locating and identifying device.

9. The system according to claim 1, wherein the external peripheral display includes a display having a convexly curved display surface turned away from a center of curvature.

10. The system according to claim 1, wherein the external peripheral display is adapted to display a criticality assessment in an event of alarm.

11. A network comprising:
two or more structures, each of the two or more structures comprising the system according to claim 1 having a respective apparatus for extracorporeal blood treatment and a respective external peripheral display, wherein the respective external peripheral displays supported by the respective apparatuses for extracorporeal blood treatment are adapted to display, in a case of alarm on plural apparatuses, alarm information to be displayed on the display surfaces of the external peripheral displays according to a priority of the alarms.

* * * * *